Figure 1:
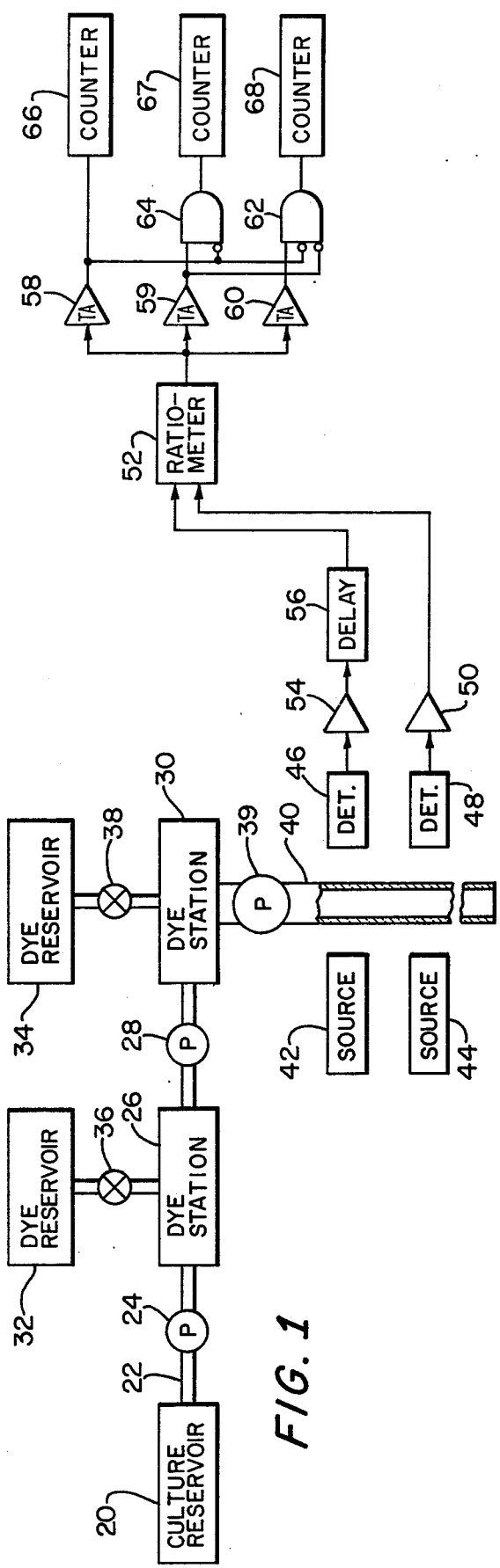

United States Patent [19]

Hirschfeld

[11] 4,025,393
[45] May 24, 1977

[54] SYSTEM FOR DETECTING GROWTH IN MICROORGANISMS

[75] Inventor: Tomas Hirschfeld, Framingham, Mass.

[73] Assignee: Block Engineering, Inc., Cambridge, Mass.

[22] Filed: Nov. 17, 1975

[21] Appl. No.: 632,244

[52] U.S. Cl. .................. 195/103.5 M; 195/127
[51] Int. Cl.² .................................. C12K 1/04
[58] Field of Search ..... 195/103.5 R, 127, 103.5 M

[56] References Cited

UNITED STATES PATENTS

| 3,551,295 | 12/1970 | Dyer | 195/103.5 R |
| 3,586,859 | 6/1971 | Katz et al. | 195/103.5 R |
| 3,864,212 | 2/1975 | Berkhan | 195/103.5 R |

OTHER PUBLICATIONS

Latt, The Journal of Histochemistry and Cytochemistry vol. 22, No. 7 pp. 478–491 (1974).

*Primary Examiner*—Alvin E. Tanenholtz
*Attorney, Agent, or Firm*—Schiller & Pandiscio

[57] ABSTRACT

A system for identifying within a mixed population, a group of microorganisms replicating in a culture medium specific to that group, which culture medium includes a fluorescence inhibitor which the group incorporates in their nucleic acid upon replication.

In one embodiment, a sample of the microorganism population is dyed with two different fluorescent dyes which are specific to nucleic acid, the fluorescent emissivity of one of the dyes being reduced or quenched by the presence of the inhibitor in the dyed nucleic acid, the fluorescent emissivity of the other of the dyes being unaffected by the presence of the inhibitor. The ratio of intensities of the fluorescent emission from the two dyes is independent of the total nucleic acid content of each microorganism, but is dependent upon the extent of incorporation of the inhibitor into the nucleic acid, so serves as a marker or identifier of a replicated organism.

In another embodiment of the invention, the sample of the population is dyed with but the one quenchable dye and the dyed organisms are exposed to high intensity radiation which very rapidly bleaches the dye. From the bleaching characteristics such as the time required for the fluorescent emission to decay from its initial intensity to l/e, or from the ratio of the initial intensity of emission to the integrated emission during bleaching, one can determine independently of the total amount of nucleic acid, changes in the quantum efficiency of the dye caused by the incorporation of the inhibitor in the nucleic acid, thereby identifying replicating organisms.

15 Claims, 3 Drawing Figures

SYSTEM FOR DETECTING GROWTH IN MICROORGANISMS

This invention relates to microbiology, and more particularly to identification and classification of organisms based upon replication of nucleic acids.

A common cytological clinical procedure for detecting and identifying a particular species or organism, such as a type of bacteria, in a sample, is simply to observe the growth of the organism in a specific culture medium. Typically, bacterial identification can be made on the basis of a growth/no-growth pattern in a set of different culture media. Typically, classical methods based on colony observation may require incubation times in excess of 24 hours and involve a minimum of 20 to 30 successive cell replications. Such procedures are frequently not clinically satisfactory because of the time lag required for growth of the organism to an observable concentration. For example, bacterial meningitis is easily treated if a proper bacteria-specific antibiotic is employed, but by the time the organism can be detected in the usual culture, the patient's prognosis has become very poor.

The term "organism" as used herein is intended to refer to unicellular micro-organisms such as fungi, bacteria, protozoa, rickettsia and the like in which chromosomal replication occurs, as well as viruses and other nucleic-acid-replicating particles which may or may not exhibit metabolic activity.

A system for culturing organisms in a medium so that they can be detected in but one generation is disclosed by Samuel A. Latt, *Microfluorometric Analysis of Deoxyribonucleic Acid Replication Kinetics and Sister Chromatid Exchanges in Human chromosomes*; J. Histochem. and Cytochem., Vol. No. 7, pp. 478–491, 1974. Latt suggests growing organisms in media containing 5-bromodeoxyuridine (BrdU) so that replicating organisms will incorporate the BrdU into their chromosomal DNA. At pH 7, the BrdU incorporated into the DNA depresses (by a factor of four relative to normal DNA) the emission of fluorescence of bisbenzimidazole dyes (such as 33258 Hoechst) bound to the DNA. Latt shows that at pH 3, the bound BrdU does not cause relative quenching; thus, he teaches that a comparison of fluorescence observed at both pH values can be used to differentiate newly grown cells from the original inoculum. However, the Latt technique does not appear to be adaptable for rapid automatic clinical detection. In any event, in automatic clinical apparatus, such as a flow cell counter, it is quite inconvenient and difficult to achieve an accurate change in pH by the successive counter stations.

Optimum procedure for detecting replication clinically is that which would operate with a delay of only the time period required to provide a single replication of the pertinent organism. A flow cell counter, i.e. a device which flows fluid in a liquid medium seriatim along a restricted channel, can detect very low cell concentrations. Thus, even the concentration of an original inoculum can be counted along with any increase in the population by replication. However, such population increases alone is not a particularly dependable or sensitive method for detecting growth of a particular species of organism, since the initial population will almost always contain a large excess of other organisms for which the culture medium is not specific. In the replicating species forms only a small part of the original population, then several generations may be required until the new growth constitutes a statistically significant percentage change in the population.

A principal object of the present invention is therefore to provide a system for detecting newly grown organisms dependently of the presence of extraneous, non-replicating organisms in the population. Another object of the present invention is to provide such a system in which even the first generation of replicating organisms is readily detectable in low porportion.

Generally, the detecting system of the present invention is based upon the incorporation of a fluorescent quenching agent or inhibitor from a culture medium into the replicating DNA (or RNA as the case may be) of the pertinent organism. The organism incorporating the inhibitor is then subsequently stained with a fluorescent dye that is specific (i.e. will bind preferentially) to the particular nucleic acid of that organism, the emission from which dye will be depressed (i.e. quenched or inhibited) by the inhibitor incorporated into the dyed nucleic acid.

Two alternative techniques can be used with respect to the organism which has been dyed with the first dye. In a first of these techniques, the organism is dyed with a second fluorescent dye which specifically bonds to the organism's nucleic acid, which second dye is selected from those dyes which are substantially not affected by the presence of the fluorescence inhibitor. The dyeing of the nucleic acid with the first and second dyes can take place simultaneously if the dyes are compatible or the dyeings can be achieved serially, the order of dyeing being largely a matter of choice provided that the dyes do not compete with one another, transfer energy between themselves, or that the first dyeing does not saturate the dyeable sites on the nucleic acid. This can readily be accomplished with low dye loading. The organisms dyed with the two dyes are then illuminated with radiation at fluorescence excitation wavelengths of the dyes to be excited into fluorescence. Measurement is made of the ratio of intensities of the fluorescent emission received from each of the two dyes. Of course, the two dyes must exhibit either different fluorescent excitation absorption bands or different emission bands or both, so that one can discriminate between the emissions from the dyes. Determination is then made of the ratio of the fluorescent emission intensities respectively provided by each of the dyes coupled to the nucleic acid. The ratio of fluorescent emission intensities is indepenent of the total nucleic acid content and dependent upon the fractional extent of the incorporation of the fluorescence inhibitor in the nucleic acid.

One can therefore readily distinguish between the micro-organisms of the original inoculum including parent replicating organisms and subsequent somatically divided or replicated generations of the latter, and between first generation and some of the second generation organisms. The organisms of the original inoculum (including parents) will have no fluorescence inhibitor incorporated in their nucleic acid and will therefore exhibit a fixed ratio ($a/b$) of fluorescent emission, (assuming the nucleic acid per se does not absorb energy in a same absorption band as the dyes) where $a$ and $b$ respectively are the emission intensities due to the first and second dyes. As noted, this ratio is quite independent of total nucleic acid content in each organism so should be relatively invariant for all organisms of the original inoculum. The first generation of replicating microorganisms will each have half of their nucleic acid derived from a parent free of any inhibitor agent. The other half of the nucleic acid in each of the first generation organisms, being formed from the culture medium, will incorporate inhibitor. The first generation organism will provide a ratio of fluorescent emission intensity of a/nb where $2 \geqslant n > 1$, the value of $n$ being dependent upon the effectiveness and the amount of inhibitor incorporated into the nucleic acid. One-half of the second generation organisms will have half of their nucleic acid inherited as inhibitor-free nucleic acid from a first generation organism, the other half of the nucleic acid incorporating inhibitor from the culture medium; these second generation organisms are indistinguishable from the first generation. But the other half of the second generation organisms will inherit half of their nucleic acid as inhibitor-containing nucleic acid from a first generation cell and the other half of their nucleic acid will contain inhibitor taken from the culture medium. Thus, any organisms exhibiting a fluorescent intensity ratio of a $2nb$ necessarily are second or higher generation organisms.

It will immediately be appreciated that by the foregoing system, one can readily identify even a first generation replication in a particular specific medium thereby establishing that the organism is one which will grow in the specific culture medium used. Upon identification of a replicating organism, that organism can then be segregated and further classified by other known techniques if necessary. It will be apparent that measurements of the intensity of fluorescence due to the quenchable dye in each organism alone cannot, by themselves, provide sufficient data to distinguish between variation in fluorescent intensity among the several organisms due on the one hand to a difference in DNA content (i.e. different species of organisms) and on the other hand to the success or failure of an organism to incorporate the inhibitor agent from the ambient culture medium.

The second technique of the present invention does dispense with the use of the non-quenching stain. However, after the sample of the population of organisms has been stained with a quenchable dye, the organisms are illuminated with radiation at a fluorescent excitation wavelength of the dye bound to the nucleic acid, and with an intensity sufficient to cause rapid bleaching (e.g. within several milliseconds typically) of the bound dye. Over a time interval commencing with the initial illumination of the organism, the fluorescent emission produced by the organism during bleaching of the latter is detected and summed or integrated. The integral obtained is independent of the quantum efficiency of the dye but the time required to decay to 1/e is a measure of the quantum efficiency. From a change in the ratio of peak intensity to the integrated intensity, it will be apparent that therefore one can readily distinguish between the dyed nucleic acid of the parent organism and the dyed nucleic acid of subsequent generations wherein the quantum efficiency of the dye has been necessarily impaired by the incorporation of the inhibitor agent during the replication.

Thus, briefly summarized, the invention is a system for identifying typically within a mixed population of microorganisms, a group of microorganisms replicating in a culture medium which is specific to that group, ie. in which substantially only that group can replicate, which medium includes a fluorescence inhibitor which the microorganisms of the group will incorporate into their nucleic acid during replication. In the system, a sample of the population is dyed with at least one fluorescent dye which will specifically bond to the nucleic acid of the microorganisms of the group. The fluorescent dye and the inhibitor are selected so that when the dye binds to nucleic acid which has incorporated the inhibitor, the normal fluorescence of the dye (e.g. such as would characterize the same dye bound to nucleic acid free of the inhibitor) will be inhibited. The dyed nucleic acid is then stimulated into fluorescent emission and a measurement is made of at least two different fluorescent emissions from the sample (e.g. emission from the one fluorescent dye at different times in one case, and emission from the one fluorescent dye and from yet another fluorescent dye in the second case). The two emissions are so selected that a mathematical function (e.g. a ratio and the like) of parameters of the two emissions is a value substantially independent of the total nucleic acid content of each of the microorganisms in the sample, but instead is dependent substantially only on the fractional extent of incorporation of the inhibitor into nucleic acid during replication.

Figure 2:
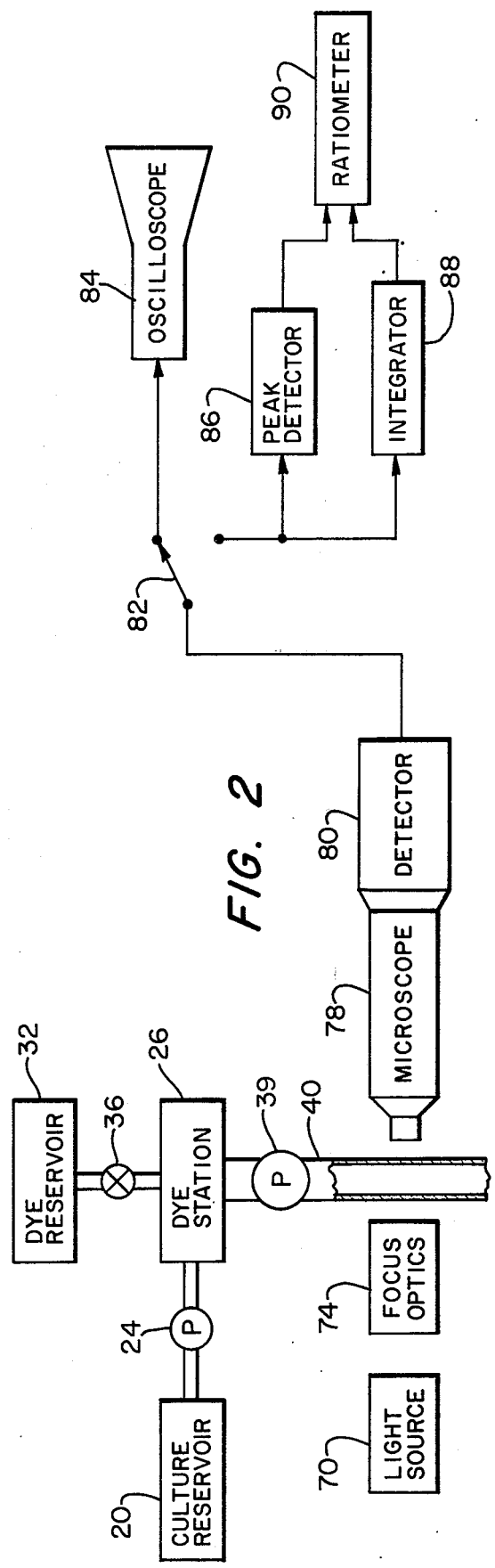
Figure 3:
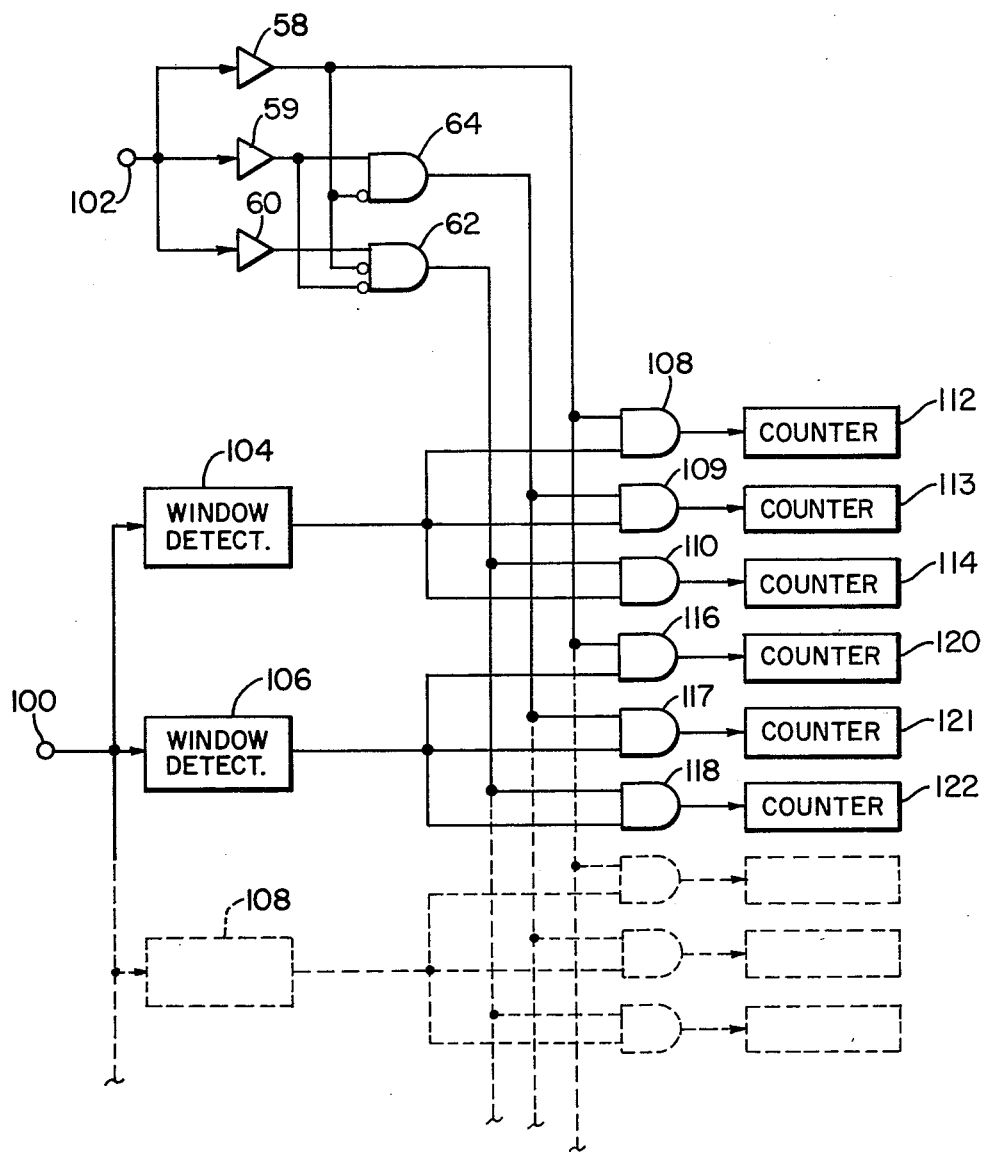

Other objects of the present invention will in part be obvious and will in part appear hereinafter. The invention accordingly comprises the apparatus and method possessing the construction, combination of elements, and arrangement of parts which are exemplified in the following detailed disclosure, and the scope of the application of which will be indicated in the claims. For a fuller understanding of the nature and objects of the present invention, reference should be had to the following detailed description taken in connection with the accompanying drawings wherein:

FIG. 1 is a schematic diagram, partly in block, of exemplary apparatus embodying the principles of the present invention; and FIG. 2 is another schematic diagram showing an alternative embodiment of the apparatus embodying the principles of the present invention; and FIG. 3 is a schematic diagram of additional circuitry useful in conjunction with the embodiments of FIGS. 1 and 2 for correlating patterns of growth with different organisms.

As noted, the operation of the present invention depends upon the role of nucleic acids in the replication process; necessarily, interaction of both the inhibitor agent and the quenchable dye with the nucleic acid is very important. Thus, some special requirements must be met by the quenchable dye and inhibitor agent used, and a discussion of characteristics of fluorescent dyes is appropriate.

In dyes generally, the long wavelength absorption band is attributed generally to the energy transition of the dye molecule from the electronic ground state to the first excited singlet. Subsequent decay to the ground state is responsible for spontaneous fluorescence in fluorescent dyes. Among the nonradiative process that reduce fluorescent emission are those which are responsible for or promote energy transition of the molecules to the system of triplet states from which the decay to the ground state is generally nonradiative. According to K.H. Drexhage, *Dye Lasers*, p. 152, Springer-Verlag, N.Y., 1973, the rate of crossing from the singlet to the triplet manifold varies according to an empirical "loop rule". The latter states that in a dye where the $\pi$ electrons of the chromophore can make a loop when oscillating between the end groups, the triplet yield will be higher than in a related compound where the loop is blocked. The inter-system crossing rate can be greatly enhanced if a "heavy" element (i.e. an element which is heavier than either hydrogen or those elements which appear in the first row of the periodic table) is substituted into the dye, or indeed is even merely close enough to the dye to influence electron oscillation in the latter. Enhancement of the triplet yield by unblocking serves to reduce (i.e. inhibit or quench) fluorescent emission from the dye because the probability of transition from the singlet to the ground state has been reduced.

It will be appreciated that the quenchable dye employed in the present invention is a dye which meets the Drexhage loop rule in that the $\pi$ electrons of the chromophore of the dye are blocked so that they will not loop when oscillating between the end groups, but can be unblocked by the presence of a heavy atom i.e. dye fluorescent emissivity can be quenched by the presence of the "heavy" atom such as is contained in the inhibitor agent.

In addition to being a fluorescent dye in which the transition to the triplet manifold can be enhanced by the presence of a heavy element, the quenchable dyes used in the invention should also be substantially specific to a nucleic acid, either RNA or DNA. To this end, the dye should be highly cationic so that it will bind covalently to the nucleic acid. Preferably, the quenchable dye should also be a fluorochrome, i.e. exhibit a substantially enhanced fluorescent emissivity in its bound state (i.e. when bonded to an unsubstituted nucleic acid) as compared to the emissivity in the unbound state of the dye. Among the dyes which are nucleic-acid-specific and meet the requirements of the Drexhage loop rule that the molecular energy transition to the triplet manifold be enhanced by the presence of a heavy element, are such dyes as berberine sulfate (C.I. No. 75160), Methylene blue (C.I. No. 52015), thionine (C.I. No. 52000), astrazone orange R, and many others.

Additional nucleic-acid-specific, quenchable dyes are
3,3' diethyloxadicarbocyanine iodide;
3,3' diethylthiodicarbocyanine iodide;
3,3' diethyloxatricarbocyanine iodide; and
4,5,4' 5'-dibenzo-3,3' diethyl-9-methyl thiacarbocyanine iodide.

The nature of the quenching agent or inhibitor necessarily must be such that that it will be incorporated by the replicating organism into the nucleic acid of the latter without substantially interfering with the replication process itself as by poisoning or the like. Additionally, the quenching agents should be compounds to which a "heavy" element (particularly halogens other than fluorine or chlorine) can be attached so that the heavy element can serve to unblock the dye and enhance the molecular energy transition of the dye to the triplet system. Lastly, the inhibitor agent should be selected so that when incorporated into the nucleic acid of an organism, it will not interfere with the bonding between the quenchable dye and the nucleic acid.

Deoxyribonucleic acid (DNA) of all micro-organisms is believed to contain substantially only four bases substituted or unsubstituted: two purines, adenine and guanine, and two pyrimidines, thymine and cytosine, the pyrimidine-purine ratio being always unity. Ribonucleic acid (RNA) is similar to DNA but contains uracil instead of thymine. Th inhibitor agent preferably is one of the four bases, tagged with a substituted heavy atom such as iodine or bromine and distributed in the culture medium to the exclusion of the untagged base, or may be some other tagged precursor compound which will be incorporated only into the nucleic acid, the synthesis of the latter in a replicating organism. Typical examples of appropriate inhibitor agents are 2 deoxy-5-bromouridine, 2 deoxy-5-iodouridine, 2 deoxy-bromocytosine, 2-deoxyiodocytosine, and the like.

Referring now to the drawings, there will be seen in FIG. 1 an exemplary device embodying the principles of the present invention and comprising culture reservoir 20 which is typically connected by appropriate piping 22 to metering pump 24. The output of pump 24 is connected to a first container or dye station 26. Dye station 26 includes an outlet pipe connected through another pump 28 connected as an input to a second similar container or dye station 30. The device of FIG. 1 also includes first and second dye reservoirs 32 and 34. Reservoir 32 is connected through appropriate piping and valve 36 to discharge for example by gravity feed into dye station 26. Similarly, reservoir 32 is connected through appropriate pipe and valve 38 to discharge into dye station 30. Dye station 30 is also provided with an outlet connected by pump 39 to pipe 40, the latter preferably being in the form of a glass capillary 40 for confining a flow stream. Capillary 40 is internally dimensioned so that microorganisms within a predetermined size range can be expected to pass therethrough, suspended in the fluid, in seriatim flow. A number of devices using flow streams of this type are known and have been described, such as in U.S. Pat. No. 3,699,362 to Ehrlich et al.

Disposed in sequence along capillary 40 are radiation sources 42 and 44, which respectively provide selected wavelength bands of fluorescence exciting radiation (as by appropriate filtering). Disposed on the other side of capillary 40 are a pair of detectors 46 and 48, typically photoelectric, each being responsive to the selected wavelength bands provided by a corresponding one of sources 42 and 44. The detectors are positioned so that passage of a microorganism through capillary 40 between a source and a corresponding detector serves to modulate the signal from that source as seen by that detector. The output of the downstream (with respect to the direction of travel of microorganism in the flow in capillary 40) detector 48 is connected to amplifier 50, the output of the latter being connected as one input to ratiometer 52. The latter is a well-known electronic device which need not be described further here. The output of upstream detector 46 is similarly connected as an input to amplifier 54. The output of the latter is connected through an electrical delay line 56 to the latter is connected through an electrical delay line 56 to the other input of ratiometer 52. The delay period interposed to delay line 56, being intended to cause simultaneous application to the inputs of ratiometer 52 of the sequential signals due to the passage of the same microorganism past detectors 46 and 48, should be set as a function of the flow rate of the microorganisms through capillary 40. Ratiometer 52, of course, serves to provide an input signal which is a ratio of the magnitude of the two signals respectively received from detectors 46 and 48. Other systems for deriving a ratio of the two signals will be obvious to those skilled in the art. For example, in the embodiment shown, the signal ratio is provided as an analog value. The signals however can be digitized in analog-to-digital converters, the digitized numbers stored as in shift resisters, and the ratio of the stored digitized numbers can be readily computed in a simple digital arithmetic unit.

In order to discriminate among the signal ratios provided by ratiometer 52 derived from microorganisms in the original inoculum, first generation and higher generation microorganisms, the output of ratiometer 52 is connected in common to the inputs of thresholding amplifiers 58, 59 and 60. Such amplifiers, as well known in the art, can be of the type which provide an output signal in the form of a pulse only if the amplitude of the input signal exceeds some predetermined value or threshold. Consequently, amplifier 58 has its threshold set so that it will provide an output signal only if the input signal is greater in magnitude than some value which lies slightly below $a/b$ but well above $a/nb$. Similarly, amplifier 59 has its threshold set so that it will provide an output pulse if its input signal is greater than a value which lies just below $a/nb$ but well above $a/2nb$. Lastly, amplifier 60 has its threshold set so that an output pulse is provided if the input signal exceeds some value just below $a/2nb$. Obviously then a signal $a/b$ will trigger all three amplifiers to provide output pulses. Consequently, the output of amplifier 60 is coupled as one input to AND gate 62, the latter also having two inhibiting input terminals connected to the outputs of amplifers 58 and 59 respectively, Thus, if any other amplifier is triggered along with amplifier 60, gate 62 will provide no output signal, but will provide an output signal if and only if amplifier 60 has an output signal. The output of amplifier 59 is connected to an input of AND gate 64, but the latter also has an inhibiting input terminal connected to the output of amplifier 58. Thus, if amplifier 59 is triggered to produce an output pulse, gate 64 will provide an input if it has an input signal only from amplifier 59 but not if amplifier 58 is also providing an output pulse. Lastly, the output of amplifier 58 is connected to the input to counter 56, the output of gate 64 is connected to the input to counter 67, and the output of gate 62 is connected as the input to counter 68.

In operation of the device of FIG. 1, a liquid culture medium is first prepared, which culture medium is specific to the particular microorganisms sought to be identified in an inoculum. The composition and conditions for preparing such a culture medium are very well known in the art so need not be repeated here. The culture medium also includes an inhibitor or quenching agent hereinbefore described. The liquid culture medium is stored under appropriate conditions in reservoir 20, and the innoculum introduced. After some predetermined time believed sufficient to have encompassed one or more replication periods, pump 24 is activated to draw a sample from reservoir 20 and introduce it into dye station 26. A predetermined amount of solution of a quenchable dye of the type hereinbefore described is introduced into station 26 through valve 36 from reservoir 32, and the dye allowed to remain, under known dyeing conditions, in contact with the sample for some predetermined time sufficient to achieve dyeing of the nucleic acids of the microorganisms in the sample. The sample is then transferred, as by pump 28 to dye station 30 where the sample is mixed with a predetermined amount of dye solution of a non-quenchable, nucleic-acid-specific dye drawn from reservoir 34 through valve 38. Again, the sample is permitted to remain in contact with the second dye solution for a period of time sufficient to permit the second dye to bond to the nucleic acids. It should be noted that whether the dyes are applied simultaneously or sequentially, the dye concentrations should be low enough so that neither dye will saturate the nucleic acids, and the dye concentrations and dyeing conditions should be fixed for all samples drawn from a particular culture so that the ratio of dyes bound to the nucleic acid of each microorganism is substantially invariant from sample to sample thus permitting ready calibration of the apparatus.

Where the embodiment of the present invention requires the use of a second non-quenching fluorescent dye, it will be apparent that the essential parts of the dye can readily be defined. Clearly, the dye must be a fluorescent dye, preferably a fluorochrome. For convenience, the dye should be able to provide an output intensity of approximately a similar order of magnitude to that of the first or quenchable dye so that the detectors can be of approximately similar sensitivity and the resulting detector signals are not several orders of magnitude different from one another. The dye must be nucleic-acid-specific, and being "non-quenchable" should not conform to the Drexhage loop rule, i.e. its fluorescence emissivity should not be quenched or impaired by the presence of a "heavy" atom.

Among the dues which are nucleic-acid-specific and are nonquenching are such dyes as acridine orange (C.I. No. 46005), quinacrine, ethidium bromide and many others. Ethidium bromide has an optimum excitation wavelength range of 480 to 550 m and optimum fluorescent wave-length range of 580 to 650 m. The structure of EB is believed to be as follows:

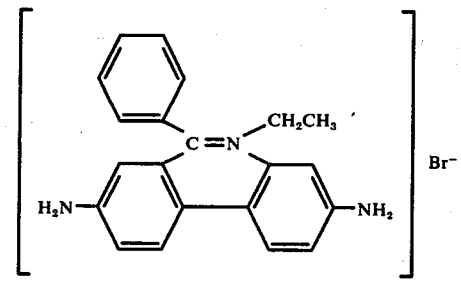

After the sample has been dyed by both dyes, pump 39 is activated to provide a flow of the dyed sample through capillary 40, at a substantially fixed flow rate. Source 42 then preferably provides output radiation in a fluorescence excitation absorption band of one of the dyes while some 44 provides radiation in a different fluorescence excitation wavelength band characteristic of the other dye. Alternatively, of course, should both dyes have substantially similar fluorescence excitation wavelengths, they would necessarily have to be distinguished by a difference in the wavelentths of their fluorescent emissions, rather than the absorption wavelengths. In either case, it is apparent that the signal seen by the detectors 46 and 48 correspond to the fluorescence emission intensity from respective ones of the dyes. The outputs of the detectors are amplified and synchronized so that a ratio of the fluorescence intensities of the two dyes can be obtained for each microorganism passing through capillary 40.

As earlier noted, because no inhibitor is present in any of the microorganisms of the original inoculum, there is no reason for the ratio of intensities to vary from one original microorganism to another notwithstanding that there may be in the inoculum many different types of microorganisms with respectively different amounts of nucleic acids. Hence, all such original microorganisms should provide maximum ratios and each such microorganism will be tallied in counter 66. However, if any microorganisms in the original inoculum could replicate in the culture medium, the first generation thereof would incorporate inhibitors in their nucleic acid and thus would each provide a fluorescent intensity ratio which would not be sufficient to trigger amplifier 58 but would trigger both amplifier 58 and 60 and be tallied in counter 67. If the incubation time in the culture medium has been sufficient to permit growth of more than one generation of the specific microorganisms, a number of the second and subsequent generations will, as noted, incorporate sufficient inhibitor in their nuclieic acid to reduce the ratio of fluorescence signal intensities to a level which will only trigger amplifier 60 and therefore be tallied or counted in counter 68.

If upon taking a sequence of samples from reservoir 20, one observes first a growth of the tally in counter 66, then a small, steady accumulation of the count in counter 67 and finally the commencement and steady growth of a count in counter 68, one can be reasonably certain that the microorganism for which the culture medium is specified, is present. Such determination can clearly be made within a short time period required for replication of but a few generations of the specific microorganisms.

A typical example of the operation of the system of FIG. 1 involves the growth of a microorganism, specifically yeast, in a growth medium containing 10% dextros, 3% yeast extract and (as an inhibitor for the culture medium) 2 deoxy-5-bromouridine added to provide a concentration of about $1 \times 10^{-5}$M. Separate, equal strength aqueous solutions are prepared of ethidium bormide (as the non-quenchable dye) and 33258 Hoechst dye (as the quenchable dye). The latter is aged in aqueous solution for several days to become a fluorochrome, apparently through hydrolysis. The structure of the 33258 Hoechst dye is as follows

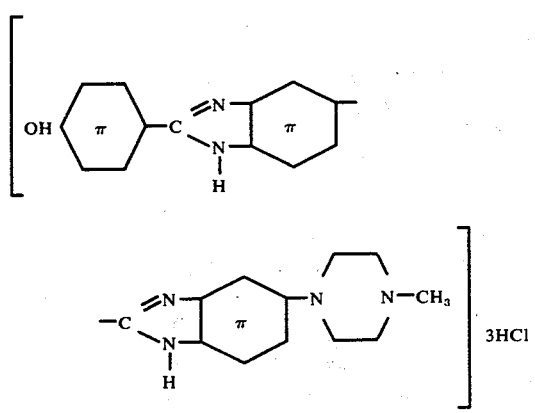

Samples of the yeast culture are subsequently dyed with the two dyes each adjusted to about $1 \times 10^{-5}$M level. The stained organisms are examined, as in the capillary flow tube, by exciting the dyes at their respective absorption maxima, using the 365 Hg line for the Hoechst dye and the blue-green continuum for the ethidium bromide. The emission maxima of the two dyes are then detected, in the red region for the ethidium bromide and in the blue-green region for the Hoechst dye. A substantial difference is obtained very quickly between the ratio of emission intensities observed for parent cells as compared to the cells of subsequent generations. Of particular interest, since yeast replicates by budding, in many instances one can observe visually by microscope the Hoechst dye fluorescence from a mother cell with an attached budding daughter, the emission from the daughter being quite dim in comparison to the mother.

In the alternative embodiment of the invention in which the quenchable dye alone is used, as shown in FIG. 2, (wherein like numerals denote like parts) there is provided a culture reservoir 20 connected by meterius pump 24 to dye station 26. Dye reservoir 32 is provided, typically connected by gravity feed through valve 36 to dye station 26. An output conduit from dye station 26 is connected through pump 39 to transparent capillary 40.

The embodiment of FIG. 2 also includes light source 70 for producing a beam of coherent light. Although spatial coherence is not necessary, typically light source 70 can be a laser (such as that manufactured by Spectra Physics) which for example, provides a 10 mW output at the desired absorption wavelength of the dyed organisms.

Disposed in the path of radiation from source 70 is an optical train 74 typically comprising a 45X objective lens followed by an achromat lens typically having 22 mm φ and a focal length of 44 mm. Optical train 74 is intended to direct light from source 70 onto the flow stream in capillary 40. The axis of capillary 49 illuminated by source 70 is preferably disposed in the focal plane of the objective of microscope 78. The latter typically has a 4X objective lens preceeded with a diaphragm having a pinhole aperture of about 100 micron diameter. The microscope is also provided with a filter for blanking out (i.e. completely adsorbing) the specific exciting wavelengths while preferably fully transmitting the fluorescent emissions.

Disposed at the eyepiece of microscope 78 is a photodetector such as photomultiplier tube 80. for converting the amplitude of the light seen by microscope 78 into proportional electrical signals such as voltages. The output of photomultiplier tube 80 is connected to switch 82 which alternatively connects the output of tube 80 to one of two different measuring systems. A first measuring system simply is here shown as resettable storage type cathode ray oscilloscope 84 such as Textronix Type 546B which serves to store the signal from photomultiplier tube 80. The time varying trace presented on the face of storage oscilloscope 84 can readily be permanently recorded, as by a camera.

A second measuring system comprises a peak detector circuit 86 having its input connected in parallel to the input of integrator circuit 88, both inputs being connectable through switch 82 to the output of dectector 80. Peak detector circuit 86 preferably includes means, such as a sample-and-hold circuit at its output, for synchronizing output signals from the peak detector circuit with output signals from integrator circuit 88. The outputs of both circuits 86 and 88 are connected to respective inputs of ratiometer 90.

The basis behind operation of the system of FIG. 2, described in more detail in my U.S. patent application Ser. No. 633010 filed concurrently herewith, is as fol- lows: when a fluorescent molecule is studied under very high steady state illumination (e.g. greater than 100 watts/cm² for fluorescein) such as will typically be required for extreme sensitivity work, the fluorescent molecule will be repeatedly excited at very short intervals and will spend an appreciable fraction of the time in the excited state. Under these conditions, the susceptability of such an excited state to decomposition by photolysis or by other chemical reactions becomes very important. In other words, intense illumination tends to produce a rapidly fading fluorescent emission, or bleaching, as the molecules decompose. The total energy emitted by the excited molecules will then be a function of the initial emitted fluorescent power (determined by the number of fluorescent molecules present, the illumination intensity and the quantum efficiency of the fluorescent molecules) and of the decomposition lifetime of the molecule. Integration of this function to the point of complete bleaching shows the total emitted energy to be proportional to the product of the quantum efficiency and the decomposition lifetime. The decomposition lifetime must necessarily be inversely proportional to the fraction of the time that the molecule spends in the excited state, and this fraction of time in turn is proportional, for any given illumination intensity to the lifetime of the molecular excited state.

Thus, if we consider the proportionality of the lifetime of the mean molecule in its excited state ($\tau_L$) with the bleaching lifetime ($\tau_B$) (i.e. the amount of time required to effect substantially complete bleaching of a plurality of the dye molecules under given illumination intensity), we note that the product of the quantum efficiency times the bleaching lifetime is a constant. Bleaching can be considered complete when output radiation of fluorescent emission is substantially non-detectable or below the noise of the detection system.

Inasmuch as the total amount or number of photons which are emitted by an excited population of a given number of particular dye molecules is a constant, if one measures the integral of the entire output fluorescence during the bleaching lifetime of the dye, one obtains thereby the maximum signal that one can possibly get from that population. Thus, one first illuminates the dyed cell with radiation at an excitation wavelength at an intensity sufficient to cause bleaching. Time of exposure of material to such radiation can run from a few milliseconds to as much as a few hundred milliseconds for practical purposes, but need only be a substantial fraction (i.e. > ½) of the bleaching lifetime. While the fluorescing cell is exposed to the excitational illumination, the instantaneous flourescence emission intensity is detected and a measurement is made of the time interval required for the fluorescent intensity to decay during bleaching, from its initial intensity $I_o$ to some predetermined fraction of the intensity, e.g. $I_o/e$ where $e$ is the Naperian base. The time interval thus measured is proportional to the bleaching lifetime and hence the quantum efficiency of the dye. If successive measurements of bleaching lifetime show a change, it is apparent that the change is due to incoporation of inhibitor in the organism's nucleic acid.

In operation of the apparatus of FIG. 2, successive samples of dyed organisms passing through capillary 40 are exposed to radiation or bleaching intensities and the intensity of the resultant fluorescent signal detected an monitored over a variable time period established from initial emission to a time when the intensity has decayed to a predetermined fraction of its original value. Flow rate in capillary 40 should be slow enough to permit substantially complete bleaching to occur while each organism remains in the focus of microscope 78. The signal observed by photomultiplier 80 when connected by switch 82 to oscilloscope 84 is displayed and observed on oscilloscope 84 along a horizontal time axis appropriately time calibrated. The initial intensity is observed and then the intensity after a limited period of time is observed. From the intensity increment of decay and the time required for that decay increment to occur, the bleaching lifetime $\tau_B$ (arbitrarily established as the time required for the initial intensity I to decay to I/e) can be readily deduced, although the bleaching lifetime of course can also be defined, if one wishes, as any multiple or submultiple of I/e as recognized by those skilled in the art.

To integrate total emission during $\tau_B$, assuming that the oscilloscope trace is long enough, the point on the time axis at which the initial intensity $I_o$ has fallen to I/e (i.e. $I_t$) is determined and the area under the curve between Io and $I_t$, is then measured. It will also be recognized that the integral of the decay curve is the mirror image of the latter so that the integral can either be directly measured or can readily be computed from the decay curve.

If the oscilloscope trace is too short, then one may use the well-known decay equation:

$$I_t = I_o e^{-K \Delta t}$$

(where
$I_o$ = initial intensity at a starting time $t_o$
$I_t$ = intensity after some later time $t_1$
$t = t_1 - t_o$
$k = 1/\tau_B$
$e$ = the Naperian base, and
$\tau_B$ = bleaching lifetime)

By measuring $I_o$, $I_t$ and $t$ one can solve for K and hence the value of $\tau_B$.

Alternatively, when switch 82 connects the output of detector 80 to the input of detector circuit 86, the latter measures and holds the peak value of th fluorescent intensity seen for an organism by microscope 78 while the entire fluorescent signal produced during bleaching is integrated in integrator 88. The value of the integral is independent of quantum efficiency of the dye; the peak value of intensity depends upon quantum efficiency and is sensitive to quenching. The ratio of the two values is therefore a normalized measure of the quantum efficiency which ignores variations in the intensity of light source 70, concentration of dyes and the like.

The principles of the present invention, as noted, can detect the presence of the very small proportion of growing organisms in a mixed culture. It is therefore possible to use the pattern of such growth for each individual organism in different media to identify the organism or to provide susceptibility measurements with respect to the media.

In order to determine, organisms by organism, the growth pattern across a set of media the various species of oganisms must be differentiated as their growth (or nongrowth) in each medium is determined. This can be accomplished by sorting out or classifying the organisms in several nucleicacid size classes according to the amount of nucleic acid in each organism, classifying the organisms according to growth classes and correlating the growth classes with each size class of organism.

The amount of nucleic acid in each organism can be readily determined in accordance with the value of the signal at the output of amplifier 50 in FIG. 1 (assuming that source 44 provides the requisite excitation wavelengths for the unquenchable nucleic-acid specific dye with which the organism is stained) or by the value of the integral provided at the output of integrator 88 in FIG. 2 (in the event that the microorganism is only dyed with the quenchable, nucleic-acid specific dye).

It is estimated that, based upon the range of nucleic acid contents in microorganisms from virions to eucaryotes, one could easily provide as many as 170 classes or bins for arranging a microorganism population according to that nucleic acid content. The system for classifying organisms according to growth has already been described, particularly in connection with the apparatus of FIG. 1. To correlate nucleic acid content with growth, one may either "window" measurements for the specific DNA content ranges of interest, or use a multichannel analyzer to give curves for generations as a function of DNA content. In some cases, the value of daughter-parent ratio or grandaughter-daughter ratios to be compatible with a constant generation time can serve to detect the overlap of two simultaneously growing populations in a curve. In other cases, the variations of parent population in a bin can be used to detect overlap between two non-simultaneously growing populations in a bin.

Apparatus for carrying out the method of detecting the presence of a small population of growing organisms in a mixed culture is shown schematically in FIG. 3 wherein two input terminals 100 and 102 are provided. As indicated above, terminal 100 is intended to be coupled to the output of amplifier 50 (in the case of a system using both a quenchable and an unquenchable dye as in FIG. 1) assuming that the output of amplifer 50 represents the signal dye to the unquenchable dye. Where terminal 100 is connected to the output of amplifier 50, then terminal 102 would be connected to the output of ratiometer 52. Alternatively, terminal 100 can be connected to the output of integrator 88 of FIG. 2, in which case the output of ratiometer 90 would be connected to terminal 102. In both cases, it will be seen that terminal 100 is connected to a source of a signal which is dependent upon the amount of nucleic acid in the organism and unaffected by the presence of absence of a fluorescence inhibitor in the nucleic acid. Similarly, the signal at terminal 102 represents a ratio which is completely independent of the nucleic acid in the organism being examined, but which does vary in accordance with the amount of fluorescence inhibitor incorporated in the nucleic acid.

As shown in FIG. 3, terminal 102 is connected in common as inputs to threshholding amplifiers 58, 59 and 60, and exactly as shown in FIG. 1, the outputs of amplifiers 58, 59 and 60 are coupled to gates 62 and 64. Terminal 100 is connected in common to the inputs of a plurality of window detectors 104, 106 and 108, the latter being shown in phantom to indicate that the number of window detectors is a matter of choice and is established according to the number of "bins" to which one wishes to classify the microorganisms accoridng to nucleic acid content. Window detectors are typically circuits, well known in the art, (such as that described by J. Markus in Electronic Circuits Manual, McGraw Hill Book Company, 1971 at page 930) which can be set to provide an output signal if and only if the input signal lies between a pair of limits respectively representing an upper and lower limit on nuleic acid content. Thus, window detector 104 and window detector 106 are set to provide an output signal if and only if the input signal represents respective different ranges of nucleic acid content. The output of window detector 104 is connected in common to three AND gates 108, 109 and 110. Another input to AND gate 108 is connected to the output of amplifier 58. The output of gate 64 is connected as another input to gate 109, and the output of gate 62 is connected as another input to gate 110. The output of gates 108, 109 and 110 are respectively connected as inputs to counters 112, 113 and 114.

Similarly, the output of window detector 106 is connected in common as an input to AND gates 116, 117 and 118. The output of amplifier 58 is also connected as another input to gate 116. The outputs of gates 64 and 62 are respectively also connected as other inputs to gates 117 and 118. The output of gates 116, 117 and 118 are connected as inputs to counters 120, 121 and 122.

It will be seen then that in the circuit of FIG. 3, the output of amplifier 58 and gates 64 and 62 which respectively represent three different generations, are logically summed with the outputs from each of the window detectors 104, 106, etc. by virtue of AND gates such as 108, 109, 110 and the like, thereby correlating nucleic acid content with growth. The resulting correlations are stored in the corresponding counters 112, 113, 114, etc. which serve as bins.

Since certain changes may be made in the above apparatus and method without departing from the scope of the invention herein involved, it is intended that all matter contained in the above description or shown in the accompanying drawing shall be interpreted in an illustrative and not in a limiting sense.

What is claimed is:

1. Apparatus for identifying within a mixed population of microorganisms, a group of microorganisms replicating in a specific culture medium in which only said group can replicate, said medium including a fluorescence inhibitor which said group will incorporate within its nucleic acid during replication, and which will inhibit the normal fluorescent emission from at least one selected fluorescent biological dye capable of bonding to said nucleic acid, said apparatus comprising in combination:

means for dyeing a sample of said population with said selected fluorescent dye;

means for exciting fluorescent emissions from the dyed sample; and means for measuring the intensities of at least two different fluorescent emissions from said dyed sample upon excitation thereof and means for determining the ratio of said intensities, said ratio being a value substantially independent of the total nucleic acid content of each of said microorganisms and dependent substantially only upon the fractional extent of incorporation of said inhibitor into nucleic acid during said replication.

2. Apparatus as defined in claim 1 including means for dyeing said sample with a second fluorescent dye which specifically bonds to said nucleic acid, said second dye being selected so that said inhibitor incorporated within nucleic acid dyed by said second dye does not substantially inhibit fluorescent emission from said second dye upon excitation of said second dye; and wherein said means for exciting fluorescent emissions includes means for exciting said emissions from both of said dyes; and wherein said means for measuring includes means for measuring the fluorescent emissions from both of said dyes.

3. Apparatus as defined in claim 1 wherein said means for measuring includes means for detecting and intergrating the intensity of fluorescent emissions from said dye during a time interval commencing with initial illumination with said radiation and continuing during bleaching of said dye, and means for measuring the initial intensity of fluorescent emission due to said initial illumination, said means for determining said ratio including means for correlating measurement of the initial intensity of fluorescent emissions with the integral obtained by said means for integrating.

4. Apparatus as defined in claim 1 wherein at least one of said emissions is so selected that its intensity is dependent upon the total nucleic acid content of the microorganism from which said one emission arose, said apparatus including means for correlating said value of said function with said intensity of said one emission.

5. Apparatus as defined in claim 1 including means for correlating measurement of said intensities with said ratio.

6. In a method of identifying, in a mixed population of microorganisms, a group of microorganisms grown in a culture medium in which substantially only said group of microorganisms can replicate, the nucleic acid of a sample of said group being thereafter dyed by at least one fluorescent dye, said medium containing an inhibitor agent which said organisms of said group incorporated into their nucleic acid during replication, said agent and said dye being selected so that upon stimulation by radiation normally capable of exciting fluorescent emissions from said dye, the emission from said dye bound to nucleic acid containing said agent will be inhibited, the improvement comprising the step of:

measuring the intensities of at least two different fluorescent emissions from said microorganisms of said sample upon stimulation thereof by exciting radiation, determining a ratio based on the two different emissions, said ratio being a value substantially independent of the total nucleic acid content of the microorganisms of said population and dependent substantially only upon the fractional extent of incorporation of said agent into nucleic acid during replication.

7. Method as defined in claim 6 including the steps of dyeing said sample with a second fluorescent dye which specifically bonds to said nucleic acid, said second dye being selected so that its fluorescent emission is substantially not inhibited by said inhibitor incorporated within said nucleic acid; and illuminating said sample with radiation at fluorescent excitation wavelengths of each of said first and second dyes; and said step of measuring comprising measuring the fluorescent emission intensity produced in response to said radiation from each of the dyes bonded to microorganisms in said sample.

8. The method as defined in claim 7 wherein the step of determining said ratio of the fluorescent emission intensities is of the emission from both said two dyes.

9. The method as defined in claim 6 including the steps of sequentially selecting in time several samples of said population, and measuring said two different emissions for each of said samples.

10. The method as defined in claim 6 wherein said step of measuring includes the steps of illuminating said sample with radiation at a fluorescent excitation wavelength of said one dye and at an intensity sufficient to cause bleaching of said dye bonded to said nucleic acid, and detecting the fluorescent emission produced by said dye during bleaching thereof by said radiation over a time interval commencing with initial illumination of said sample.

11. The method as defined in claim 10 including the steps of integrating over said interval the total intensity of emission detected during said interval, and determining said ratio as the ratio of the integral of said total intensity and the initial intensity detected of said fluorescent emission with respect to one another.

12. Method as defined in claim 10 including the step of measuring the time required for the initial intensity of said fluorescent emission to decay to some arbitrary fraction of said initial intensity.

13. The method as defined in claim 12 wherein said fraction is $I/e$, $I$ being said initial and $e$ being the Naperian base.

14. Method as defined in claim 8 including the step of comparing measurement of fluorescent emission intensity from the second fluorescent dye bound to each organism in the sample so as to classify said organism according to the amount of nucleic acid contained therein.

15. The method as defined in claim 6 wherein both of said emissions are dependent upon the amount of nucleic acid content in each said microorganism and only one of said emissions is independent of the amount of inhibitor agent in each said microorganism, and including the step of correlating the measured intensity of said one emission with said ratio.

* * * * *

UNITED STATES PATENT OFFICE
CERTIFICATE OF CORRECTION

PATENT NO. : 4025393
DATED : May 24, 1977
INVENTOR(S) : Tomas Hirschfeld

It is certified that error appears in the above-identified patent and that said Letters Patent are hereby corrected as shown below:

Please cancel claim 4 in its entirety.

Claim 13, line 2, (column 16, line 38) the word "intensity" should be inserted after "initial".

On the cover sheet at end of Abstract,
"15 claims" should read -- 14 claims --.

Signed and Sealed this thirtieth Day of August 1977

[SEAL]

Attest:

RUTH C. MASON
Attesting Officer

C. MARSHALL DANN
Commissioner of Patents and Trademarks